US00PP15666P2

(12) United States Plant Patent

Bessho et al.

(10) Patent No.: US PP15,666 P2
(45) Date of Patent: Mar. 15, 2005

(54) *CALIBRACHOA* PLANT NAMED 'KAKEGAWA S70'

(50) Latin Name: *Calibrachoa species*
Varietal Denomination: Kakegawa S70

(75) Inventors: Masao Bessho, Kakegawa (JP); Toshimi Ohga, Kikugawa (JP)

(73) Assignee: Sakata Seed Corporation, Yokohama (JP)

( * ) Notice: Subject to any disclaimer, the term of this patent is extended or adjusted under 35 U.S.C. 154(b) by 39 days.

(21) Appl. No.: 10/780,285

(22) Filed: Feb. 17, 2004

(51) Int. Cl.[7] ..... A01H 5/00
(52) U.S. Cl. ..... Plt./263
(58) Field of Search ..... Plt./322

*Primary Examiner*—Kent Bell
(74) *Attorney, Agent, or Firm*—Jondle & Associates P.C.

(57) ABSTRACT

'Kakegawa S70' is a new variety of *Calibrachoa* plant. This new variety has yellow petal lobes and dark green foliage.

1 Drawing Sheet

Genus/species: *Calibrachoa* species.
Varietal denomination: 'Kakegawa S70'.

BACKGROUND OF THE INVENTION

'Kakegawa S70' originated from a hybridization made in October 1999 in Kakegawa, Japan. The female parent was a *Calibrachoa* breeding line with rose colored flowers and a creeping habit known as 9B-68A (not patented). The male parent was a *Calibrachoa* named 'Sunbelki' (U.S. Plant Pat. No. 11,558).

In February 2000, $F_1$ seed from this cross was sown and later transplanted outdoors in Kakegawa, Japan. The $F_1$ plants ranged from rose to deep red in flower color and all were erect in habit. Four, single-plant selections were made from the $F_1$ generation based on their rose flower color and intercrossed to produce an $F_2$ generation. In August 2000, $F_2$ seed was sown and later transplanted outdoors in Kakegawa, Japan. $F_2$ plants ranged in color from rose to deep red to yellow to off-white and were either mounding or creeping in habit. Three, single-plant selections were made from the $F_2$ generation based on their yellow flower color and semi-creeping habit. In May 2001, these three selections were evaluated in 9 cm pots as well as in an open field. One of the selections was chosen based on trial results.

The selection was subsequently named 'Kakegawa S70' was asexually reproduced by stem cuttings in Salinas, Calif. and was determined to reproduce true to type in successive generations of asexual propagation.

DESCRIPTION OF PHOTOGRAPH

This new *Calibrachoa* plant is illustrated by the accompanying photograph which shows blooms and foliage of the plant in full color. The colors shown being as true as can be reasonably obtained by conventional photographic procedures.

DESCRIPTION OF THE GENUS *CALIBRACHOA* LLAVE & LEX

Figure 1:
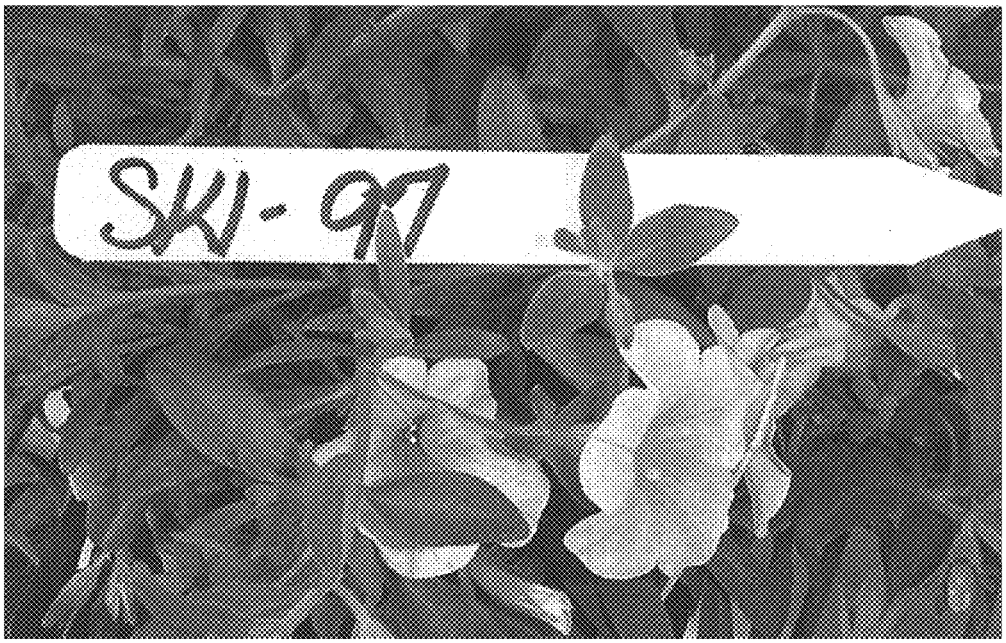
FIG. 1 shows a close-up view of flowers (known as SK1-97 during testing).
Figure 2:
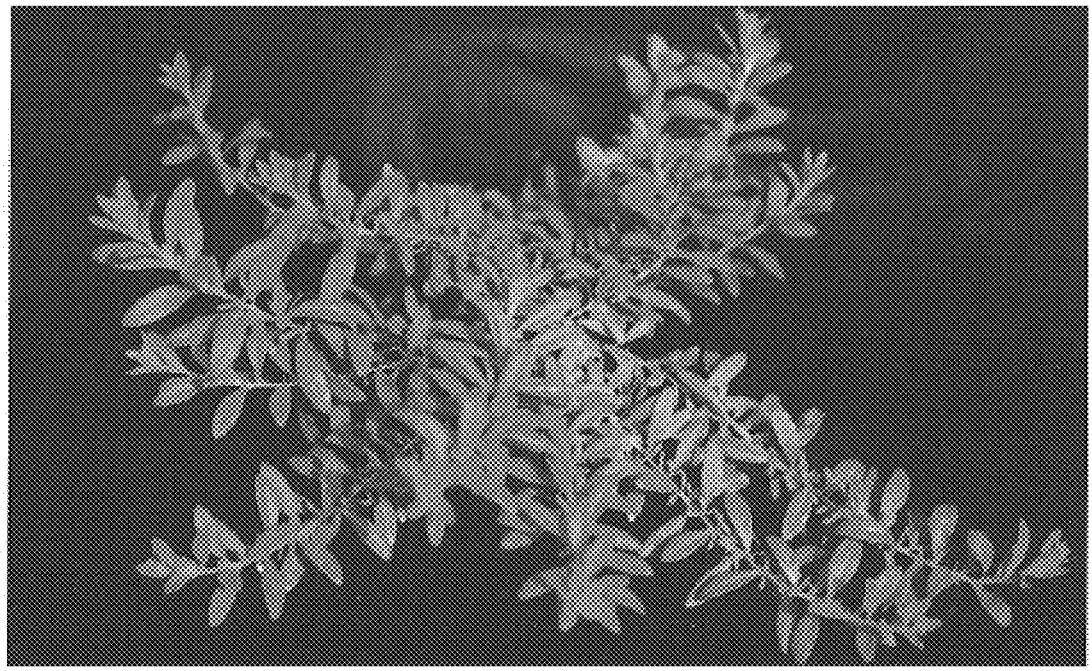
FIG. 2 shows a vegetative plant without flowers.

The genus *Petunia* was originally established in 1803 by A. L. Jussieu, who described both *P. parviflora* and *P. nyctaginiflora* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida,* the Garden *Petunia,* and the inter-relationship of several species classified as *Petunia*. These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the *Petunia* genus, Wijsman and J. H. de Jong proposed transferring the 14 chromosome species to the genus *Stimoryne*. Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990, Wijsman had transferred several species, including *P. parviflora* (=*C. parviflora*) to *Calibrachoa,* originally established by Llave and Lexarza in 1825. *Calibrachoa parviflora* (=*C. mexicana* Llave & Lexarza) is now the type species for the genus *Calibrachoa.*

Classification of the current *Petunia* and *Calibrachoa* species is still in progress. New species are also being identified. Consequently, a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, a single outermost petal covers the other four, radially folded and terminally contorted petals. *Calibrachoa* flower buds are flat with all five petals linearly folded and the two lower petals form a cover around the three other petals and fused together.

In U.S. Plant Pat. No. 11,558, the Genus for 'Sunbelki' was identified as *Petunia*. Since that time, as discussed above, the inventors have learned that the Genus *Petunia* has been split by the I. N. G., and this particular variety, because of its chromosome number and bud aestivation is more accurately characterized as a member of the *Calibrachoa* Genus.

ENVIRONMENTAL CONDITIONS FOR PLANT GROWTH

The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 DIP 'N GROW:9 water) root-inducing solution immediately prior to sticking into the cell trays. Cuttings were stuck into plastic cell trays having 98 cells and containing a moistened peat moss-based growing medium. The cuttings were misted with water from overhead for 10 seconds every 30 minutes until sufficient roots were formed.

Rooted cuttings were transplanted and grown in 20 cm diameter plastic pots in a glass greenhouse located in Salinas, Calif. The pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

DETAILED DESCRIPTION OF THE NEW PLANT

The data below was collected on plants three months from rooted cutting. The following traits and characteristics describe the new variety. Color references are to The R.H.S. Colour Chart of The Royal Horticultural Society of London (R.H.S.). The following traits and characteristics describe the new variety.

Classification:
- *Family.*—Solanaceae.
- *Species.*—*Calibrachoa* sp.
- *Common names.*—*Calibrachoa.*

Parentage:
- *Female parent.*—Breeding line 9B-68A (not patented).
- *Male parent.*—'Million Bells Yellow' (U.S. Plant Pat. No. 11,558).

Growth:
- *Habit.*—Semi-creeping.
- *Height.*—23.0 cm.
- *Spread.*—115.0 cm.
- *Life cycle.*—Tender perennial.
- *Form.*—Branching, dense.
- *Time to produce a rooted cutting.*—6 weeks.
- *Time to bloom from propagation.*—10 weeks.
- *Flowering requirements.*—Will flower so long as day length is greater than 12 hours and temperature exceed 13° C.
- *Resistance/susceptibility.*—Excellent resistance to rain, heat and drought. Will not tolerate temperatures below 10° C. Plants are susceptible to Botrytis, powdery mildew, various stem and root rots, and certain viruses, like Tobacco Mosaic Virus and Impatiens Necrotic Spotted Virus. Plants can be infested with aphids, leafminer, whitefly and various Lepidoptera.

Stems:
- *Stem color.*—RHS 144B (yellow-green).
- *Anthocyanin color.*—RHS N77A (purple).
- *Pubescence.*—Heavy.
- *Pubescence color.*—Clear.
- *Stem description.*—Round, ancipital.
- *Stem length.*—2.0 cm–2.5 cm.
- *Stem diameter.*—2.0 mm.
- *Internode length.*—1.5–2.5 cm.

Leaves:
- *Leaf arrangement.*—Alternate.
- *Leaf shape.*—Elliptical.
- *Leaf tip.*—Mucronate.
- *Leaf base.*—Decurrent.
- *Leaf margin.*—Entire.
- *Leaf surface.*—Rough, dull.
- *Leaf length.*—2.5 cm.
- *Leaf width.*—0.5 cm.
- *Leaf color.*—Upper: RHS 137A (green); lower: RHS 139B (green).
- *Leaf fragrance.*—Absent.
- *Leaf surface pubescence.*—Slight.
- *Leaf surface pubescence color.*—RHS N155A (white).
- *Petiole length.*—2.0 mm.
- *Petiole color.*—RHS 138B (green).
- *Venation.*—Pinnate.

Flowers:
- *Inflorescence type.*—Solitary.
- *Flowering habit.*—Indeterminate.
- *Duration of flower life.*—5 days.
- *Shape.*—The flowers are funnel shaped with five fissures and a shallow, yet prominent, indentation of the petal tip at the midvein.
- *Calyx.*—5 sepals, free.
- *Sepal shape.*—Lanceolate.
- *Sepal apex.*—Mucronate.
- *Sepal margin.*—Entire.
- *Sepal color.*—RHS 143A (green).
- *Flower diameter.*—2.5 cm.
- *Flower depth.*—2.2 cm–2.4 cm.
- *Floral tube length.*—1.6 cm–1.8 cm.
- *Floral tube diameter.*—0.5 cm.
- *Bud surface.*—Pubescent.
- *Bud shape.*—Ovate.
- *Bud length.*—1.0 cm—1.2 cm.
- *Bud diameter.*—0.2 cm —0.3 cm.
- *Bud color.*—RHS 199B (greyed-brown).
- *Peduncle color.*—RHS 144B (yellow-green).
- *Ovary.*—Superior.
- *Pistil number.*—1.
- *Stigma color.*—RHS 150C (yellow).
- *Style color.*—RHS 149B (yellow-green).
- *Corolla.*—5 petals, fused, diameter 2.5 cm.
- *Petal pubescence.*—Glabrous.
- *Stamens.*—Free.
- *Petal size.*—1.0 cm×1.5 cm.
- *Petal shape.*—Spatulate.
- *Petal apex.*—*Truncate.*
- *Petal margin.*—*Entire.*
- *Petal color.*—Lobes upper; RHS 7A (yellow) with RHS 154C (yellow-green) petal midveins; Lower: RHS 9A (yellow) with RHS 154C (yellow-green) petal midveins; Corolla tube: inner RHS 9A (yellow) with RHS 154C (yellow-green) veins; outer RHS 9D (yellow) with RHS 154C (yellow-green) veins.
- *Stamen number.*—5, free.
- *Stamen color.*—RHS 150C (yellow-green).
- *Pollen color.*—RHS 9A (yellow).
- *Fragrance.*—Absent.
- *Seed production.*—None.

COMPARISON WITH MOST SIMILAR VARIETY

'Kakegawa S70' is a distinct variety of *Calibrachoa* owing to its semi-creeping growth habit. 'Kakegawa S70' is most similar to the variety 'Kakegawa S27' (U.S. Plant Pat. No. 13,004); however, there are differences as shown in Table 1 below.

TABLE 1

| | 'Kakegawa S70' | 'Kakegawa S27' |
|---|---|---|
| Habit | Semi-creeping | Creeping; strongly branching |
| Petal Color | Upper petal color is RHS 7A (yellow) with a RHS 154C (yellow-green) midvein and RHS 9A (yellow) inner corolla tube. | Upper petal color is RHS 6D (yellow) fading to 8D (yellow) with an RHS 7A (yellow) corolla tube. |

Some differences between 'Kakegawa S70' and its parental lines are shown in Table 2 below.

TABLE 2

| Characteristic | 'Kakegawa S70' | Male Sunbelki | Female (9B-68A) |
|---|---|---|---|
| Petal Color | Yellow | Yellow | Rose |
| Habit | Semi-creeping | Semi-decumbent | Creeping |

What is claimed is:

1. A new and distinct cultivar of *Calibrachoa* plant as shown and described herein.

* * * * *